(12) United States Patent
Tsai et al.

(10) Patent No.: US 7,307,150 B2
(45) Date of Patent: Dec. 11, 2007

(54) DEXTRAN-HEMOGLOBIN CONJUGATES AS BLOOD SUBSTITUTES

(75) Inventors: Sheung Pun Tsai, Hong Kong (CN); Jeffrey Tze-Fei Wong, Hong Kong (CN)

(73) Assignee: Dextrosang Corporation, Ontario (CA)

( * ) Notice: Subject to any disclaimer, the term of this patent is extended or adjusted under 35 U.S.C. 154(b) by 132 days.

(21) Appl. No.: 10/975,324

(22) Filed: Oct. 28, 2004

(65) Prior Publication Data

US 2005/0113289 A1   May 26, 2005

Related U.S. Application Data

(63) Continuation of application No. 10/128,950, filed on Apr. 24, 2002, now abandoned, which is a continuation of application No. PCT/CA01/01329, filed on Sep. 19, 2001.

(30) Foreign Application Priority Data

Sep. 19, 2000   (CA) .................................. 2319966

(51) Int. Cl.
*A61K 38/42* (2006.01)
*C07K 17/10* (2006.01)

(52) U.S. Cl. ...................................... 530/385; 530/402

(58) Field of Classification Search ................... 514/6, 514/8, 59; 530/385, 402
See application file for complete search history.

(56) References Cited

U.S. PATENT DOCUMENTS 4,064,118 A * 12/1977 Wong ......................... 530/385
4,857,636 A * 8/1989 Hsia ........................... 530/385

OTHER PUBLICATIONS

Caron, A. et al "The effects of stroma-free and dextran-conjugated hemoglobin . . . " Artif. Cells Blood Subs. Immob. Biotech. (1999) vol. 27, No. 1, pp. 49-64.*
Menu, P. et al "Human hemoglobin conjugated to carboxylate dextran . . . " Artif. Cells Blood Subs. Immob. Biotech. (1994) vol. 22, No. 3, pp. 543-549.*
Bonneaux, F. et al "Fixation of various aldehydic dextrans onto human hemoglobin . . . " J. Prot. Chem. (1995) vol. 14, No. 1, pp. 1-5.*

* cited by examiner

*Primary Examiner*—Leigh C. Maier
(74) *Attorney, Agent, or Firm*—McHale & Slavin, P.A.

(57) ABSTRACT

An hemoglobin (Hb)-Dextran (Dx) conjugate having a molecular weight between 50 kd and 500 kD provides a blood substitute that results in acceptable erythrocyte sedimentation rate (ESR) and excretion rate (EXC) values. DxHb conjugates of the invention can be used for a variety of purposes as an alternative to blood.

4 Claims, 5 Drawing Sheets

Appendix I The Size Dependence of ESR and Exe. for DxHb

DEXTRAN-HEMOGLOBIN CONJUGATES AS BLOOD SUBSTITUTES

CROSS REFERENCE TO RELATED APPLICATION

This application is a Continuation of U.S. application Ser. No. 10/128,950, filed Apr. 24, 2002, now abandoned, which is a Continuation of International Application PCT/CA01/01329, with an international filing date of Sep. 19, 2001, published in English under PCT Article 21(2), which claims priority under Canadian Application No. 2,319,966, filed Sep. 19, 2000.

FIELD OF THE INVENTION

This invention relates to blood substitutes, and methods of their preparation. More particularly, the invention relates to improved polysaccharide-hemoglobin conjugates for use as a blood substitute for mammals and to methods of their preparing such conjugates.

BACKGROUND OF THE INVENTION

In recent years the quest for a safe blood substitute has accelerated rapidly. The demand often exceeds the supplies of blood available from human donors. In addition, in many parts of the world, the whole blood supply can be hazardous. Therefore, there is a need to develop blood substitutes.

One of the most important functions of blood is to carry oxygen from lungs to support tissue respiration. Hemoglobin (Hb) is an attractive oxygen carrier in the development of a clinical blood substitute, given its attributes as a respiratory pigment of extensive solubility, uptake and release of oxygen, and above all its capability of transporting a large quantity of oxygen. However, one fundamental disadvantage of free Hb itself as a blood substitute arises from its relatively small molecular size of 64.5 kD and consequent high renal excretion rate (EXC) thereby leading to a rapid clearance from the circulation. Therefore, covalent conjugation to carrier polymers has been applied in order to prevent renal excretion of Hb and to prolong its plasma half-life. Such conjugates are referred to as hemoglobin based oxygen carriers (HBOC). Examples of such polymers include: dextran and biopolymer derivatives of dextran, inulin, hydroxyethylstarch, polyethylene glycol, polyvinylpyrrolidone (S.P.Tsai and J. T.-F. Wong, Dextran-Hemoglobin, in: Winslow, R. N., Vandegriff, K. D., and Intaglietta, M. [eds.], 1997 Advances in Blood Substitutes: Industrial Opportunities and Medical Challenges, Birkhauser, Boston; the contents of these references are incorporated herein by reference).

The efficiency of oxygen delivery is determined by the total blood flow and volume, oxygen content, red cell or hemoglobin mass, oxygen affinity and the rate of oxygen consumption. The relationships between oxygen content, delivery and utilization are best exemplified by the Fick's equation. It is therefore apparent that a blood substitute which can carry and deliver a maximal amount of oxygen per unit volume, while maintaining excellent rheologic characteristics, would be ideal.

Dextran-hemoglobin (DxHb) is one of the conjugates that has been proposed as a blood substitute. The combination of water solubility, availability in a wide range of molecular sizes, and lack of significant toxicity or tissue tropism, renders dextran an excellent drug carrier among biodegradable polymers. Covalent conjugation of dextran (Dx) to hemoglobin (Hb) increases the effective size of Hb and, therefore, reduces its excretion rate (EXC) through the renal system. Methods to stabilize the viscosity of the conjugate solution have been proposed, and exchange transfusions with DxHb in dogs and macaques performed (Tam et al, 1976, Tam et al, 1978, Wong 1988). However, hitherto the flow properties of the conjugate have not been investigated.

Examples of DxHb conjugates are provided in U.S. Pat. Nos. 4,064,118 and 4,650,786, the contents of which are incorporated herein by reference. The '118 patent teaches a composition useful as a blood substitute or blood extender which is prepared by chemically coupling hemoglobin (Hb) with dextran (Dx) having a molecular weight of from about 5 kD to 2000 kD. The molecular weight of this DxHb conjugate is in the range of 70-2000 kD. It has however been found that, as compared to hemoglobin, the products according to U.S. Pat. No. 4,064,118 tend to show a somewhat greater affinity for oxygen, but retain the essential oxygen transporting and releasing capability of hemoglobin.

U.S. Pat. No. 4,650,786 describes a modified dextran-hemoglobin complex having reduced oxygen affinity. The molecular weight of this DxHb complex is in the range of 70-2000 kD.

One of the problems associated with DxHb complexes, or modified DxHb complexes, is that the viscosity of the conjugate solution increases on storage thereby rendering the solution unsuitable for administration. The solution to the above problem is described in U.S. Pat. No. 4,900,816, the contents of which are incorporated herein by reference. It has been shown that the activated sites on the dextran moiety may be blocked, and the viscosity on storage stabilized, without affecting the oxygen transport properties of the hemoglobin complex. U.S. Pat. No. 4,900,816 teaches a compound having a molecular weight from about 70 kD to about 200 kD, comprising a hemoglobin residue, an oxygen affinity reducing ligand, a polysaccharide (e.g. dextran), covalently bonded chemical bridging groups and a blocked activating group.

As indicated above, one of the important characteristics of a blood substitute is its rheological properties—in order for the substitute to be physiologically acceptable, its viscosity must not be so high as to hinder flow of blood. Although aggregation of red blood cells is one of the important causes of increased blood viscosity, especially at lower shear rates, the actual mechanism of red cells aggregation is still not completely elucidated. Aggregation of red cells can be brought about by various means. In general, both the viscosity and the RBC aggregation increase with increasing concentration of immunoglobulin; however, the exact relationship between the two appears to be quite complex. It is therefore important to characterize the possible physico-chemical properties of DxHb in its development as blood substitute.

As described below, in the present invention, various preparations of DxHb were synthesized and the rheologic properties of these solutions were examined by measuring their viscosities and their aggregating tendencies which were assessed based on erythrocyte sedimentation rate (ESR) test (Dintenfass 1985, the contents of which are incorporated herein by reference). The presence of macromolecules over a certain "critical concentration" in plasma could induce red blood cell (RBC) aggregation and in turn blood viscosity particularly at low shear rate.

Blood flow in low shear regions, especially in the venous circulation, is greatly reduced by the enhancement of erythrocyte aggregation which increases blood viscosity and impedes capillary flow through sludge formation (Dintenfass 1981). Red blood cell, RBC, aggregation is the result of bridging by macromolecules between adjacent erythrocyte surfaces. When a non-encapsulated hemoglobin-based blood substitute is infused into the circulation, these macromolecules could also interact with erythrocytes and induce RBC aggregation, with ESR being one of the foremost blood rheological parameters to be influenced by such aggregation. Therefore, it is of fundamental interest to examine the ESR enhancement effects of hemoglobin-based blood substitutes in the course of their design and development.

It is known that molecular size is one of the critical determinants of ESR enhancement through the macromolecular bridging mechanism. Dextrans of 20 kD do not induce RBC aggregation and hence, no ESR elevation, but dextrans larger than 40 kD are entirely capable of enhancing ESR (Chien and Jan 1973; the contents of which are incorporated herein by reference). Previous studies showed that macromolecular polymerized hemoglobin larger than 220 kD would induce RBC aggregation, which may increase low-shear-rate blood viscosity and affect the RBC distribution in the circulation (Tsai and Wong 1996; the contents of which are incorporated herein by reference).

The present invention provides a DxHb conjugate having a molecular weight range that results in low EXC and ESR levels and, therefore, provides an effective blood substitute or plasma expander.

SUMMARY OF THE INVENTION

The present invention, in one embodiment, provides an oxygen carrying compound comprising a conjugate of hemoglobin covalently joined to a polysaccharide, the conjugate having an average molecular weight of from about 50 kD to about 500 kD.

In another embodiment, the invention provides a method for preparing an oxygen carrying compound, the compound comprising a conjugate of hemoglobin covalently bound to a polysaccharide, the method comprising:

1) reacting the polysaccharide with a bromine compound to provide bromine groups on the polysaccharide, thereby providing an activated polysaccharide;

2) filtering the activated polysaccharide with a first filter;

3) reacting the activated polysaccharide with hemoglobin thereby providing a coupled dextran-hemoglobin molecule;

4) filtering the dextran-hemoglobin molecule with a second filter.

BRIEF DESCRIPTION OF THE DRAWINGS

These and other features of the preferred embodiments of the invention will become more apparent in the following detailed description in which reference is made to the appended drawings wherein.

DESCRIPTION OF THE PREFERRED EMBODIMENTS

Figure 1:
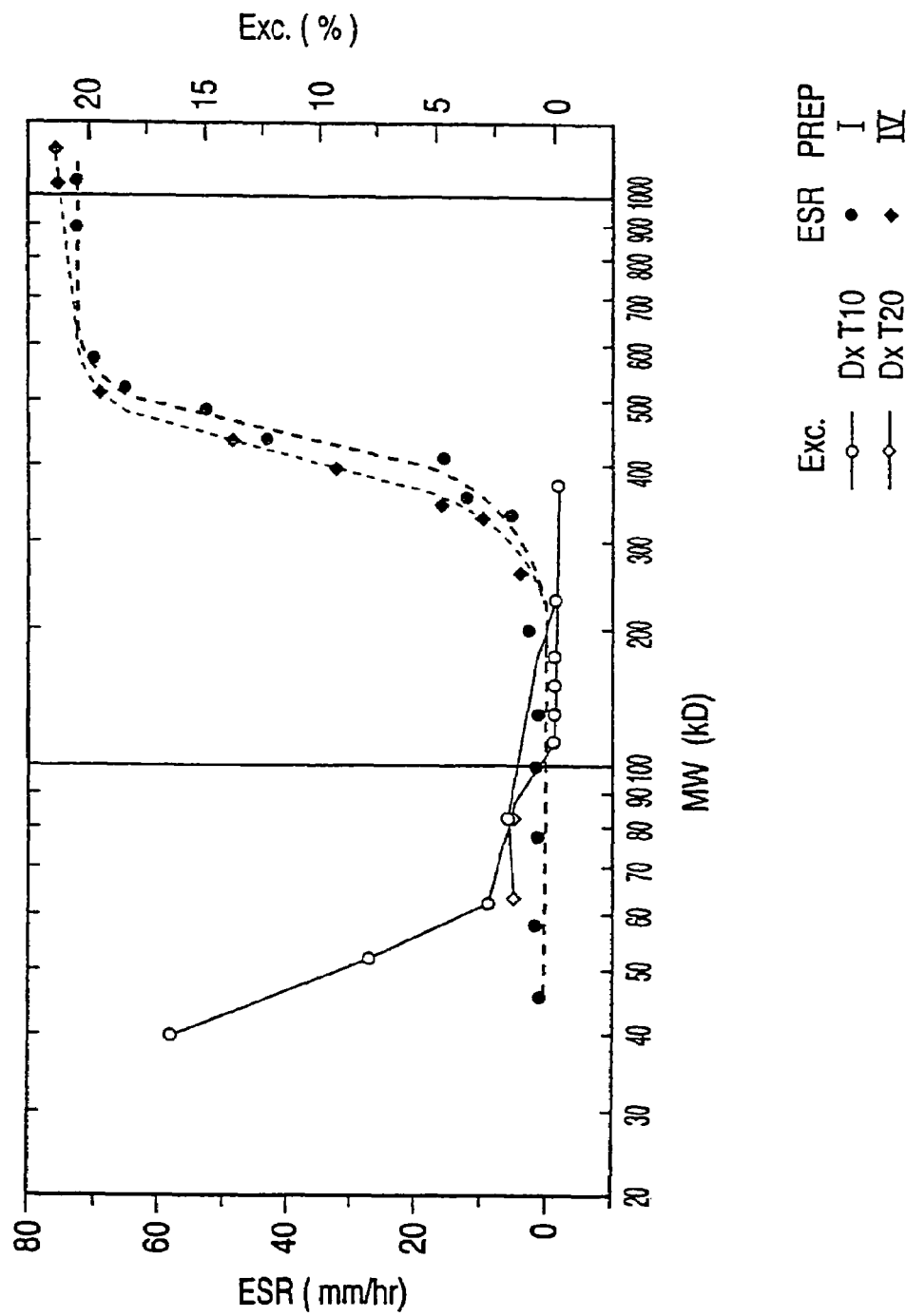
FIG. 1 illustrates the size dependence of erythrocyte sedimentation rate (ESR) and excretion rate (EXC) for dextran-hemoglobin synthesized from dextran molecules of two starting sizes, 10 kD (DxT10) and 20 kD (DxT20).

As used herein, the term "hemoglobin" will be understood to comprise hemoglobin derived from red blood cells of any mammal. Although primarily directed to human hemoglobin, the invention is equally applicable to hemoglobin derived from other animals and includes bovine and porcine hemoglobin.

In a preferred embodiment, the present invention provides a carrier polysaccharide-hemoglobin conjugate and, more preferably, an improved dextran-hemoglobin (DxHb) conjugate for use as a blood substitute or a HBOC. As discussed further below, the DxHb conjugate has, according to a preferred embodiment of the invention, a molecular weight (MW) of from about 50 kD to about 500 kD, and, more preferably, from about 89 kD to 116 kD. This range of molecule size is based primarily on the amount of conjugation between the Fb and the Dx molecules due to the fact that the size of the Hb is generally constant. This range of conjugate size has been found to provide a molecule that is sufficiently larger than Hb in size so that the EXC rate of such molecule is not high, while also providing a molecule that is sufficiently small in size so that the ESR for such molecule is also not high. As described further below, the term "high" in relation to EXC rate is 1% and that for ESR is 20 mm/hr. The invention also provides a method for production of such conjugate. The examples contained herein are provided for illustrative purposes alone and are not meant to limit the scope of the invention as will be apparent to persons skilled in the art.

1. Preparation Of Stroma-Free Human Hemoglobin (SFH)

A pure hemoglobin solution was produced by lysing red blood cells and releasing hemoglobin for use in the process of the present invention. These preparations are then processed to remove stroma in the solution so as to avoid renal damage. A hemoglobin solution with a high degree of purity was prepared according to the preferred embodiment of the present invention by standard techniques of filtration as described by Winslow and Chapman (Meth. Enzymol., 1994, 231:3-16), the contents of which are incorporated herein by reference.

2. Activation Of Dextran By The Alkylation Method

As discussed above, covalent conjugation of polysaccharides to hemoglobin increases its effective size thereby preventing its renal excretion. The polysaccharides of the present invention are of established biocompatibility and are capable of being bound to hemoglobin. The preferred polysaccharide of the present invention is dextran.

The dextran of the present invention may have an average molecular weight of 10 kD (referred to as Dextran T10) to 20 kD (referred to as Dextran T20). It should be noted that commercially available dextran is categorized by its average molecular weight and a variation in the size of the dextran molecules is inherent. It is speculated that there is higher renal as well as non-renal excretion of DxHb when 10 kD dextran is used. Therefore, the most preferred starting size for dextran is 20 kD according to the preferred embodiment of the present invention.

To modify dextran to become capable of reacting with hemoglobin it has to be "activated", preferably with by an alkylation reaction. Specifically, the dextran was reacted with cyanogen bromide (CNBr) at alkaline pH and subsequently with diaminoethane. The resultant aminoethylamino-dextran was dialysed. This dialysis step is used to wash away small reactant molecules or reacted residual substances, such as diaminoethane.

Following this, the aminoethylamino-dextran was then acylated with bromo-acetylbromide at neutral pH, and was subsequently subjected to dialysis against water and lyophilization. This process for dextran activation is described in more detail by S. C. Tam, J. Blumenstein and J. T. F. Wong, Proc. Natl.Acad.Sci. USA, 1976, 73:2128-2131; the contents of which are incorporated herein by reference.

Two tests, ninhydrin and silver nitrate tests, were used to monitor the completeness of the dialysis. Specifically, these tests were conducted on the filtrate from the dialysis step whereby the presence of amino groups was detected by the ninhydrin test as described by S. Moore and W. H. Stein (J. Biol. Chem., 1948, 176:367-388; the contents of which are incorporated herein by reference). The silver nitrate test was conducted to detect the presence of bromo groups, as discussed below. Both of these tests are further described below.

3. Preparation Of Dextran-Hemoglobin Conjugates

The final step of coupling hemoglobin to dextran was performed by adding stroma-free hemoglobin to the activated dextran, referred to as N-bromo-acetylamino-ethylamino-dextran (DxBr). The coupling reaction comprises the removal of the-Br groups of the activated dextran (DxBr) and the removal of the-H atoms of the sulfhydryl (-SH) groups of hemoglobin, allowing for the binding of Dx-to the HbS-to result in DxHb. The linkage between the bromo-aminoethylaminodextran (DxBr) and Hb is mediated through the free —SH at β-93 cysteine, the position of the covalent linkage. In the course of the coupling reaction, the-Br is detached from DxBr and becomes free Br ion, which is later dialysed away. The silver nitrate test (described further below) can be used to test for the presence of the Br ion.

The conjugation of dextran to hemoglobin was performed according to S. C. Tam, J. Blumenstein and J. T. F. Wong (Proc. Natl. Acad. Sci. USA, 1976, 73:2128-2131, the contents of which are incorporated herein by reference). According to the preferred embodiment of the present invention, the conjugation reaction was performed by mixing DxBr and stroma-free hemoglobin in an aqueous solution comprising 0.33% DxBr and 1% stroma-free hemoglobin solution. Such concentrations of Hb and DxBr ensures a DxHb coupling of 3:1 by weight or 1:1 by molar mass ratio. However, other initial concentrations of the reactants to achieve these ratios will be apparent to persons skilled in the art.

Experimentation with coupling (i.e. conjugation) of the bromo-dextran (DxBr) with a solution of higher concentration of hemoglobin resulted in a higher degree of cross-linkage, and therefore, higher molecular weight of the resultant conjugates. Therefore, in order to have a higher proportion of relatively small DxHb molecules, it is preferred that the coupling reaction take place using lower (i.e. 1%) concentrations of Hb. However, it will be understood that it is possible to perform coupling of DxBr with hemoglobin of either higher or lower than 1% concentration.

The coupling reaction was conducted in a solution having a pH of 9.5 with sodium bicarbonate buffer. The solution mixture was first sterilized with a 0.22 μm filter and the coupling reaction was allowed to proceed at 4° C. overnight, according to the method described by H. Xue and J. T. F. Wong (Meth. Enzymol, 1994, 231:308-322, the contents of which are incorporated herein by reference). The coupling reaction was allowed to proceed for about 10 to 16 hours, and most preferably for 16 hours. The longer coupling time resulted in DxHb of higher average molecular weight due to higher degree of cross-linking.

β-mercaptopropionic acid was then added to react with any residual bromo groups on the DxBr thereby stopping the coupling reaction. Further, the cross linking reaction was also stopped with this addition thereby preventing any further elevation in the solution viscosity (S. P. Tsai and J. T. F. Wong, In-Winslow, R. W., Vandegriff, K. D. and Intaglietta, M.(Eds.), Advances in Blood Substitutes, 1997, Birkhauser, Boston, the contents of which are incorporated herein by reference). The solution was then subjected to dialysis against phosphate buffered saline to clear any residual reactants and reaction by-products.

Thus, the alkylation method resulting in the above conjugation can be summarized as follows (as shown in Blumenstein et al., Experimental Transfusion of Dextran-Hemoglobin, (1978); the contents of which are incorporated herein by reference):

1) Dx+CNBr→activated Dx
2) Activated Dx+diaminoethane→aminoethylamino-dextran
3) Aminoethylamino-dextran+bromoacetylbromide→N-bromo-acetylaminoethylamino-dextran
4) N-bromo-acetylaminoethylamino-dextran+hemoglobin-SH→hemoglobin-S-acetylaminoethylamino-dextran 4. DxHb Fractionation and Correlation Between ESR, EXC and MW Fractionation steps were introduced after a discovery of the ESR enhancement by excessively large DxHb molecules. In order to determine the correlation between molecule size and ESR and EXC, the DxHb was synthesized preferably from dextran molecules of at least two starting average sizes, 10 kD (DxT10) and 20 kD (DxT20). The resultant conjugates, DxT10Hb and DxT20Hb, were fractionated using the Waters 650E Advanced Protein Purification System. More specifically, the fractionation was carried out on a Hiload™ 26/60 Superdex™ 200 prep grade gel filtration column (Pharmacia). A solution of 10 mM phosphate buffered saline, pH 7.4, was used as the elution buffer and the elution flow rate was 0.5 ml/min. The sample used was 8 ml of 8% DxHb. The fractions were collected using an ISCO Retriever II (fractions were collected for 8 min., i.e. 4 ml per fraction). The fractions were tested for ESR and EXC as discussed below. However, since the amount of sample that is obtained from the column fractionation step is insufficient for both ESR and EXC tests, the fractions from several runs were pooled and concentrated with a Centriprep 30 (Amicon) in order to have enough sample (of each size) to conduct both tests. The average MW of each fraction was also determined. Although the above mentioned fractionation step is described in relation to DxHb, it will be appreciated by persons skilled in the art that such fractionation step may also be performed on the DxBr precursor molecule. In this case, the DxBr fractionate is conjugated to Hb using the above mentioned process to result in DxHb fractions of the desired size range. The details of the measurements performed according to the preferred embodiment of the present invention are described below.

4.1. ESR Measurements

The erythrocyte sedimentation rate (ESR) is a means of quantifying the aggregation of red blood cells. Such aggregation is generally caused by the presence of macro-molecules. For this measurement, the sample is preferably prepared by mixing a 6.0% test solution with an equal volume of freshly withdrawn citrated rat whole blood. ESR measurement should be conducted within 3-4 hours after withdrawing fresh blood due to the potential changes in the suspension stability and erythrocyte deformability of red blood cells over prolonged standing. This finding was made when using blood extracted from the rat. ESR measurements were conducted in accordance with instructions provided by the manufacturer, Clay Adams, Division of Becton Dickison and Company, Parisippany, N.J., 07054 USA. Solutions were kept in a vertical position in reusable Clay Adams Wintrobe Blood sedimentation tubes (115 mm long, with a 3.0 mm bore) for 60 minutes on a universal ESR rack (Chase Instruments) at room temperature (about 20-22° C.). This method is commonly referred to herein as "Wintrobe's method" and a description of this method is provided in "Introduction to Medical Laboratory Technology", Baker & Silverstein (eds.), $5^{th}$ ed., pp. 605-606, Butterworths, the contents of which are incorporated herein by reference.

The sedimentation tubes were scaled at 1 mm intervals. For some preparations, there was no clear boundary between the sediment and supernatant, but rather a gradual color change was observed in the upper part of the ESR tube. For such preparations, ESR was recorded in a range format (e.g. 1-18 mm/hr, Table 2). An acceptable ESR was taken to be 20 mm/hr.

It should be noted that other methods for measuring ESR will be apparent to those skilled in the art. For example, instead of the Wintrobe's method mentioned above, it would also be possible to use the Westergren method as described in "Introduction to Medical Laboratory Technology", Baker & Silverstein (eds.), $5^{th}$ ed., pp. 606-607, Butterworths, the contents of which are incorporated herein by reference. These methods will result in different ESR values; however, the same conclusions will be drawn as in the present case.

4.2. EXC Measurements

Excretion rate (EXC) experiments were conducted to determine the extent of renal excretion of the DxHb conjugate of the present invention. For determining the EXC, a test solution of DxHb conjugates was infused into the jugular vein of an anesthetized male Sprague-Dawley rat of an average weight of about 300-350 g. The excretion rate was estimated by determining the hemoglobin concentration in urine sample of a rat by the method described by D. L. Drabkin and J. H. Austin, (J. Biol. Chem., 1935, 112:51-65), the contents of which are incorporated herein by reference. Although the EXC value is preferably 0, an acceptable value can be taken to be less than 1%. Above this level, the urine of the rat was found to be reddish in colour.

4.3. Molecular Weight Measurements

The molecular weights of the DxHb conjugates were measured using gel filtration chromatography wherein molecules elute from the column in order of decreasing molecular weight. As DxHb molecules get fractionated over the gel filtration column, a detector monitors their retention time. Fast Protein Liquid Chromatography (FPLC) was employed for molecular weight determination of DxHb conjugates of the present invention, however High Performance Liquid Chromatography (HPLC) could be employed as well. For the purposes of illustrating the invention, molecular weights were determined using the Waters 650E Advanced Protein Purification System. The following two columns were used in series in this system: 1) the TSK-Gel GMPWXL (7.8× 300); and, 2) the Pharmacia Superose 6 HR10/30. The elution buffer consisted of 10 mM Tris-HCl, 0.05% sodium azide, pH 8.0, which was used with a flow rate of 0.4 ml/min. In the preferred embodiment, the composition of the eluent is verified using detectors that can be used for MW determination of DxHb. For example, a Wyatt Technology MiniDAWN laser detector or a UV detector could be used for this purpose. In the preferred embodiment, the following three detectors were used in series: a Waters 440 UV Detector A280; a Wyatt Technology MiniDAWN detector; and, a Waters 410 Differential Refractometer. Table 1, below, lists the peak molecular weight values of the various DxHb manufactured. Further, the following molecular weight data was obtained using the above described system:

| | Sample | Calculated Average Mol. Wt. |
|---|---|---|
| 1) | purified Hb | (66 +/− 7) kD |
| 2) | dextran T20P (DxT20P - Pharmacia) | 16.0 kD |
| 3) | activated dextran (DxBr) after filtering to obtain a filtrate with components lower than 300 kD | 24.4 kD |
| 4) | DxHb after filtering to obtain a filtrate with components less than 500 kD and then filtering to obtain a retentate with components greater than 80 kD | 115.6 kD |

Molecular weight determinations of various fractions were made by comparing the ratio of $V_e/V_o$ for the molecule in question to the $V_e/V_o$ of protein standards of known molecular weight ($V_e$ is the elution volume and $V_e$ is the void volume). The void volume of a given column is based on the volume of effluent required for the elution of a large molecule such as Blue Dextran or the like. A calibration curve can then be prepared by plotting the logarithms of the known molecular weights of protein standards versus their respective $V_e/V_o$ values.

It should be noted that measured molecular weight values can vary depending upon the equipment/methods used. For example, S. P. Tsai and J. F. T. Wong (Artificial Cells Blood Subst. Immob. Biotech., 1996, 24:513-523) reported an anomaly in measuring the molecular weight of hemoglobin. According to such report, the Hb molecule, because of its compact, round molecular structure and shape, was found to have a MW measurement of just 46 kD, as determined by FPLC system, whereas its theoretical value is 64.5 kD. As indicated above, the molecular weight measurement of Hb using the MiniDAWN laser method was found to be 66+/−7 kD giving a range of 58-73 kD, which is very near the theoretical value. Furthermore, dextran, because of its linear structure, results in a molecular weight reading using gel filtration, that is higher than its theoretical value. This fact should be taken into consideration when determining MW limits for DxHb conjugates of the present invention. For this reason, the above mentioned laser detector was used in order to obtain more accurate results. For example, using such laser detector, the measured molecular weight of Hb was found to be close to its theoretical value.

4.4. The Size Dependence of ESR and EXC for DxHb Conjugates

Data for ESR, EXC and MW as measured at the peak of the elution volume as mentioned above, are provided below in Table 1 and are illustrated in FIG. 1.

TABLE 1

The size dependence of ESR and EXC for DxHb conjugates synthesized
from dextran molecules of two starting sizes (10 kD and 20 kD)

| Elution Vol (mL) | MW (kD) | Dx(T10)-Hb ESR (mm/hr) | EXC (%) | Dx(T20)-Hb ESR (mm/hr) | EXC (%) |
| --- | --- | --- | --- | --- | --- |
| 124 | 1217 | 75 | | | |
| 128 | 1067 | 74 | | 73 | |
| 132 | 935 | 73 | | | |
| 136 | 820 | 72 | | 73 | |
| 140 | 719 | 71 | | | |
| 144 | 630 | 67 | | 70 | |
| 148 | 553 | 53 | | | |
| 152 | 484 | 43 | | 46 | |
| 156 | 425 | 13 | | 28 | |
| 160 | 372 | 8 | 0.00 | 16 | |
| 164 | 326 | 2 | | 5 | |
| 168 | 286 | 1 | | 1 | |
| 172 | 251 | | | 0.5 | |
| 176 | 220 | | 0.00 | | 0.00 |
| 180 | 193 | 0.2 | | 0.2 | |
| 184 | 169 | | | | 0.09 |
| 188 | 148 | | | 0.2 | 0.00 |
| 192 | 130 | 0.2 | | | 0.00 |
| 196 | 114 | | | | 0.00 |
| 200 | 100 | | | 0.2 | 0.56 |
| 204 | 88 | | 1.44 | | 1.34 |
| 208 | 77 | 0.2 | | | |
| 212 | 67 | | 2.85 | | 1.03 |
| 216 | 59 | | | 0.2 | |
| 220 | 52 | | 7.77 | | |
| 224 | 45 | 0.2 | | | |
| 228 | 40 | | 16.49 | | |

As discussed above, the problem of rapid excretion of hemoglobin by itself appears to be a consequence of its relatively low molecular weight In order to increase the molecular weight of hemoglobin to allow for adequate retention, it is coupled to a polysaccharide such as dextran or the like. Ideally, no renal excretion of hemoglobin should be observed if such hemoglobin is administered in the form of DxHb conjugates as a blood substitute. However, an excretion rate lower than about 1%, and more preferably lower than about 0.2%, is preferred (S. C. Tam and J. T. F. Wong, Impairment of Renal Function by Stroma-Free Hemoglobin in Rats, J. Lab. Clin. Med, 1988, 111:189-193; the contents of which are incorporated herein by reference).

As also discussed above, although a higher molecular weight leads to reduced EXC, such larger molecules result in an increased ESR. According to the preferred embodiment of the present invention, ESR should be less than about 20 mm/hr, and, more preferably, the ESR should be less than about 1 mm/hr.

After the DxHb conjugates of the present invention were fractionated on the basis of molecular weight using gel filtration chromatography and the collected fractions were tested for their effect on the ESR, it was found that DxHb fractions with peak molecular weights less than about 500 kD did not enhance ESR over the acceptable limit of up to 20 mm/hr. On the other hand, DxHb conjugates greater than peak molecular weight of about 50 kD resulted in an EXC value within the acceptable range of between 0 and 1%. According to the preferred embodiment of the present invention, the results define an acceptable range of molecular weight for DxHb conjugates of about 50 kD to about 500 kD that results in the desired levels of EXC and ESR.

5. Selection For The Optimal Fractionation Procedure To Obtain Preferred DxHb Conjugates Once the above desired molecular weight range of DxHb conjugates was determined, the search for the optimal fractionation procedure was launched. One factor to consider in determining an optimal fractionation procedure is the maximization of the yield of the DxHb product. A high yield of the final product avoids any unnecessary waste of the DxHb.

Several methods were employed to achieve the goal of obtaining the final DxHb products of the optimal molecular size. These methods included ethanol precipitation, choice of the starting dextran, and filtering. Fractionation of Dx, DxBr and DxHb was done before and after the activation step, as well as before and after the conjugation step to screen for a better production scheme. The procedures employed, and the resulting ESR and EXC, for the various DxHb preparations are listed in Table 2 below.

TABLE 2

Erythrocyte Sedimentation Rate and Excretion Rate
of DxHb Conjugates Obtained by Various Procedures.

| # | Preparation | ESR (mm/hr) | EXC(%) | Yield DxBr | Yield DxHb | Yield Overall |
|---|---|---|---|---|---|---|
| Hb | Stroma-free Human Hemoglobin | <1 | 30-40 | | | |
| | DxHb Preparations Based on DxT20P** | | | | | |
| 1 | DxT20P, activate, <100 kD (Millipore), couple | 60 | ND* | 57 | 100 | 57 |
| 2 | DxT20P, activate, >100 kD (Millipore), couple | 78 | ND | 30 | 100 | 30 |
| 3 | DxT20P, activate, <100 kD (A/G)***, couple | 32 | ND | 38 | 100 | 38 |
| 4 | DxT20P, activate, >100 kD (A/G), couple | 50 | ND | 53 | 100 | 53 |
| 5 | DxT20P, activate, <300 kD (A/G), couple | 30 | ND | 35 | 100 | 35 |
| 6 | DxT20P, activate, >300 kD (A/G), couple | 78 | ND | 60 | 100 | 60 |
| 7 | DxT20P, activate, <500 kD (A/G), couple | 57 | ND | 49 | 100 | 49 |
| 8 | DxT20P, activate, >500 kD (A/G), couple | 64 | ND | 42 | 100 | 42 |
| | Different Filters to Fractionate DxHb After the Coupling | | | | | |
| 9 | DxT20P, activate, couple, <500 kD >70 kD (A/G) | 1-20 | ND | 100 | 49.5 | 49.5 |
| 10 | DxT20P, activate, couple, >500 kD (A/G) | 76 | ND | 100 | 33 | 33 |
| 11 | DxT20P, activate, couple, <750 kD >70 kD (A/G) | 51 | ND | 100 | 54.8 | 54.8 |
| 12 | DxT20P, activate, couple, >750 kD (A/G) | 73 | ND | 100 | 23.7 | 23.7 |
| | Selected Filters Used Before and After the Coupling | | | | | |
| 13 | DxT20P, activate, <300 kD, couple, <500 kD >80 kD (A/G) | 1 | ND | 35 | 100.2 | 35 |
| 14 | DxT20P, activate, <300 kD, couple, <500 kD (A/G) | 1 | ND | 35 | 99.2 | 34.7 |
| 15 | DxT20P, activate, <300 kD, couple, >500 kD (A/G) | ND | ND | 35 | 0.8 | 0.3 |
| 16 | DxT20P, activate, <500 kD, couple, <500 kD (A/G) | 1-18 | ND | 49 | 91.1 | 44.6 |
| 17 | DxT20P, activate, <500 kD, couple, >500 kD (A/G) | 77 | ND | 49 | 8.9 | 4.4 |
| 18 | DxT20P, activate, <500 kD, couple, <750 kD >70 kD (A/G) | 25 | ND | 49 | 86.3 | 42.3 |
| 19 | DxT20P, activate, <500 kD, couple, >750 kD (A/G) | 80 | ND | 49 | 13.7 | 6.7 |
| | Filters of Different Brands to Fractionate DxBr Made from DxT20P | | | | | |
| 20 | T20, activate, couple, >10 kD (A/G) | 76 | 0.24 | 100 | 100 | 100 |
| 21 | T20, activate, <30 kD (A/G), couple | <1 | 1.60 | 8 | 100 | 8 |
| 22 | T20, activate, >30 kD (A/G), couple | 76 | 0.30 | 85 | 100 | 85 |
| 24 | T20, activate, <50 kD (A/G), couple | 1-18 | ND | 4 | 100 | 4 |
| 25 | T20, activate, >50 kD (A/G), couple | 76 | ND | 91 | 100 | 91 |
| 26 | T20, activate, <50 kD (Microgon), couple | 1-9 | ND | 14 | 100 | 14 |
| 27 | T20, activate, >50 kD (Microgon), couple | 74 | ND | 85 | 100 | 85 |
| 28 | T20, activate, <50 kD (Paul Filtron), couple | 45 | ND | 14 | 100 | 14 |
| 29 | T20, activate, >50 kD (Paul Filtron), couple | 74 | ND | 81 | 100 | 81 |
| 30 | T20, activate, <60 kD (A/G), couple | 1-36 | ND | 18 | 100 | 18 |
| 31 | T20, activate, >60 kD (A/G), couple | 77 | ND | 82 | 100 | 82 |
| 32 | T20, activate, <70 kD (Paul Filtron), couple | 32 | ND | 17 | 100 | 17 |
| 33 | T20, activate, >70 kD (Paul Filtron), couple | 74 | ND | 82 | 100 | 82 |
| 34 | T20, activate, <100 kD (A/G), couple | 53 | ND | 22 | 100 | 22 |
| 35 | T20, activate, >100 kD (A/G), couple | 74 | ND | 73 | 100 | 73 |
| | DxHb Preparations Based on DxT10P | | | | | |
| 36 | T20, activate, couple, >10 kD (A/G) | 76 | 0.08 | 100 | 100 | 100 |
| 37 | T20, activate, couple, >30 kD (A/G) | ND | 0.07 | 100 | 99.9 | 99.9 |
| 38 | T20, activate, couple, >50 kD (A/G) | ND | 0.27 | 100 | 99.4 | 99.4 |
| 39 | T20, activate, couple, >70 kD (A/G) | ND | 0.04 | 100 | 98.4 | 98.4 |
| 40 | T20, activate, couple, >100 kD (A/G) | ND | 0.00 | 100 | 65.7 | 65.7 |
| 41 | T10, activate, couple, >10 kD (A/G) | 1-15 | 1.35 | 100 | 100 | 100 |
| 42 | T10, activate, couple, >30 kD (A/G) | ND | 0.88 | 100 | 99.8 | 99.8 |
| 43 | T10, activate, couple, >50 kD (A/G) | ND | 0.37 | 100 | 97.6 | 97.6 |
| 44 | T10, activate, couple, >70 kD (A/G) | ND | 0.23 | 100 | 95.2 | 95.2 |
| 45 | T10, activate, couple, >100 kD (A/G) | ND | 0.06 | 100 | 9 | 9 |
| 46 | T10, activate, <30 kD >10 kD (A/G), couple, >10 kD (A/G) | 1 | 2.60 | 39 | 100 | 39 |
| 47 | T10, activate, <30 kD >10 kD (A/G), couple, >30 kD (A/G) | ND | 1.56 | 39 | 99.7 | 38.9 |
| 48 | T10, activate, <30 kD >10 kD (A/G), couple, >50 kD (A/G) | ND | 0.19 | 39 | 97.9 | 38.2 |
| 49 | T10, activate, <30 kD >10 kD (A/G), couple, >70 kD (A/G) | ND | 0.21 | 39 | 90.3 | 35.2 |
| 50 | T10, activate, <50 kD (M) >5 kD (M), couple | <0.5 | 2.53 | 5 | 100 | 5 |
| 51 | T10, activate, >50 kD (M), couple | 10 | 0.47 | 66 | 100 | 66 |
| 52 | T10, activate, <60 kD (A/G) >5 kD (M), couple | <1 | 4.70 | 25 | 100 | 25 |
| 53 | T10, activate, >60 kD (A/G), couple | 35 | ND | 67 | 100 | 67 |
| 54 | T10, >50 kD (M), activate, couple | 1 | 0.18 | 66 | 100 | 66 |

TABLE 2-continued

Erythrocyte Sedimentation Rate and Excretion Rate
of DxHb Conjugates Obtained by Various Procedures.

| # | Preparation | ESR (mm/hr) | EXC(%) | Yield DxBr | Yield DxHb | Yield Overall |
|---|---|---|---|---|---|---|
| | Ethanol Used for Fractionating DxT10 | | | | | |
| 55 | T10, 0-55% ethanol ppt****, activate, <30 kD >10 kD (A/G), couple, >10 kD (A/G) | <1 | 0.41 | 45 | 100 | 45 |
| 56 | T10, 0-55% ethanol ppt, activate, <30 kD >10 kD (A/G), couple, >30 kD (A/G) | ND | 0.51 | 45 | 99.8 | 44.9 |
| 57 | T10, 0-55% ethanol ppt, activate, <30 kD >10 kD (A/G), couple, >50 kD (A/G) | ND | 0.47 | 45 | 97.9 | 44.1 |
| 58 | T10, 0-55% ethanol ppt, activate, <30 kD >10 kD (A/G), couple, >70 kD (A/G) | ND | 0.13 | 45 | 96.1 | 43.2 |
| 59 | T10, 0-55% ethanol ppt, activate, <30 kD >10 kD (A/G), couple, >100 kD (A/G) | ND | 0.00 | 45 | 40.2 | 18.1 |
| 60 | T10, 0-49% ethanol ppt, activate, couple | 62 | ND | 19 | 100 | 19 |
| 61 | T10, 49-55% ethanol ppt, activate, couple | 15 | ND | 17 | 100 | 17 |
| 62 | T10, 55-80% ethanol ppt, activate, couple | <1 | ND | 11 | 100 | 11 |
| 63 | T20, 0-46% ethanol ppt, activate, couple | 73 | ND | 40 | 100 | 40 |
| 64 | T20, 46-75% ethanol ppt, activate, couple | 23 | ND | 54 | 100 | 54 |

Where:
1) "DxT10" and "DxT20" refers to the starting size of the dextran (Dx) molecule; i.e. an average molecular weight of 10 or 20 kD, respectively.
2) "activate" means activation of Dx by alkylation as described above.
3) "couple" refers to the conjugation, or coupling, of DxBr to Hb as described above.
4) "<100 kD", or ">500 kD", or the like, refers to the cut off value of the filters used during the filtering step of DxBr or DxHb. Further, the symbols "<" and ">" refer to the values of the filtrate and retantate, respectively. For example, "<100 kD" indicates that the filter provides a filtrate containing only those molecules having a molecular weight less than 100 kD. Similarly, ">500 kD" indicates that the filter provides a retantate having molecules with molecular weights greater than 500 kD.
*ND = not determined
**all Dx samples (i.e. T10, T20, T20P) were obtained from Pharmacia Biotech AB.
***A/G = A/G Technology Corp., Needham, MA, USA
****ethanol ppt = ethanol precipitation (discussed further below)

Filters of larger cut-off sizes (e.g. 500 kD) applied after the coupling reaction assisted in eliminating the excessively large DxHb conjugates (those that are larger than about 500 kD—the upper limit for the preferred products). Intermediate filters (e.g. 50 kD, 70 kD) applied after conjugation were used to remove molecules smaller than the lower limit for preferred products (about 50 kD). The actual function of small filters (e.g. 10 kD) is the same as that of the dialysis process that is carried out after the conjugation reaction, that is to remove any residual reactants (e.g. mercaptopropionic acid etc.).

The function of the ethanol precipitation is to eliminate the excessively large dextran molecules before the activation step. Ethanol was added in a stepwise manner. For example, in preparations #55-59 (Table 2) ethanol was added slowly starting from an initial concentration of 0% up to a final concentration of 55%. As a result, some excessively large dextran molecules were precipitated, pelleted and re-dissolved for later activation.

Several preparations of DxHb were selected from the list in Table 2 as the most preferred. These preparations are identified in Table 2 as numbers: 13, 14, and 16. The choice of the selected preparations was based on the desired ESR and EXC values as well as the yield of the product.

Figure 3:
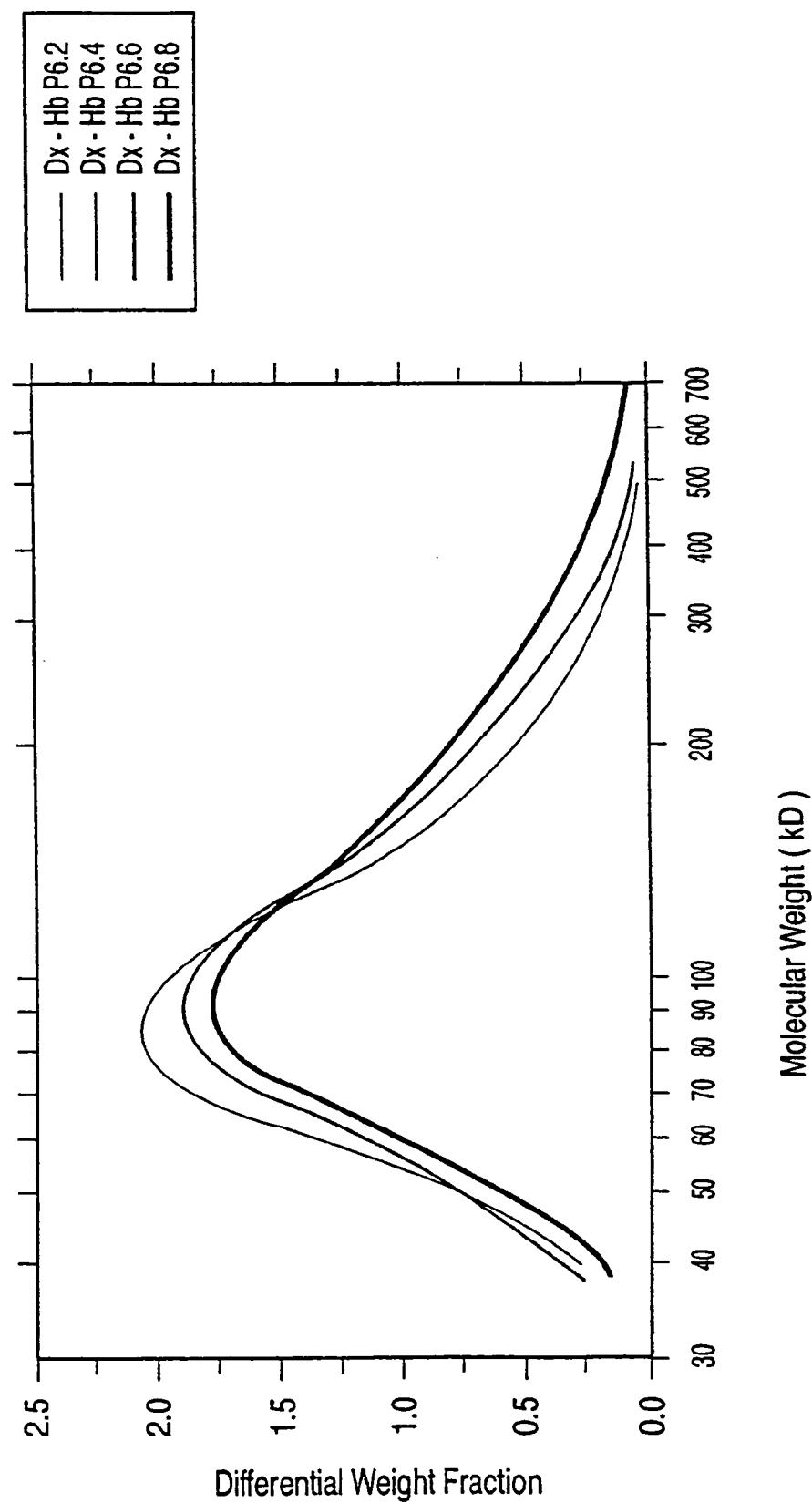
FIG. 3 illustrates a molecular weight distribution of four most preferred preparations of DxHb as measured with FPLC and MiniDawn laser detector.

Peak molecular weights for these preparations were determined as described above and are illustrated in FIG. 3. As shown in FIG. 3, the peak MW of the preferred preparations, two batches of preparation #14 and two batches of preparation #16, was found to be 102, 96, 93, 89 kD. In addition, although not shown in FIG. 3, the average MW of preparation #13 was found to be 116 kD. These numbers define the most preferred range for the average MW of the most preferred DxHb preparations of the present invention.

Thus, according to the present invention, the preferred size range of the DxHb conjugates is from about 50 kD to about 500 kD, with the most preferred range of about 89 kD to about 116 kD. The optimal procedure for synthesizing these preparations comprises the activation of dextran having a starting size of 20 kD, filtrating the activated DxBr through a 500 kD or 300 kD filter, coupling the products of filtration with stroma-free hemoglobin, filtrating the resulting DxHb through a 500 kD filter to eliminate any excessively large conjugates. The most preferred procedure for producing the DxHb conjugates of the present invention also includes a final step of filtrating the resultant conjugates through a 80 kD filter to eliminate any excessively small conjugates that might potentially increase the EXC value.

Table 3 below presents data for the preparation of DxHb conjugates that is similar to that of Table 2. However, Table 3 includes additional further preparation and analytical information concerning the various conjugates. The data in Table 3 also indicates the molecular weight distribution for the various batches.

TABLE 3

Preparation Procedures for Dx-Hb and Analytical Results:

| Batch Code | Procedures & Coupling Conditions (1) | Component Yield (2) | Lower Limit | Upper Limit | Ave MW | ESR mm/hr | % >200 kD | % >300 kD | % >400 kD | % >500 kD |
|---|---|---|---|---|---|---|---|---|---|---|
| P5.1 | DxT20P, activate, couple at 6%, >500 kD | 23.0 | 1300 | 6300 | too viscous | | 100 | 100 | 100 | 100 |
| P5.5 | DxT20P, activate, couple at 1%, >500 kD | 25.9 | 500 | 6000 | 930 | 77 | 100 | 100 | 100 | 97 |
| P5.3 | DxT20P, activate, couple at 1%, >500 kD | 6.6 | 300 | 3000 | 572 | 76 | 100 | 100 | 74 | 58 |
| P4.1 | DxT20P, activate, coupleat 6%, >750 kD | 30.2 | 220 | 3000 | 490 | 73 | 100 | 82 | 65 | 53 |
| P4.3 | DxT20P, activate, coupleat 6%, >750 kD | 14.9 | 350 | 3000 | 778 | 73 | 100 | 100 | 95 | 84 |
| P1.1S | DxT20P, activate, couple at 6%, <750 kD | 83.3 | 100 | 2000 | 207 | 70 | 53 | 34.5 | 22.5 | 15 |
| P3.2 | DxT20P, activate, couple at 6%, <500 kD, >70 kD | 46.5 | 80 | 1800 | 160 | 63 | 39 | 23 | 14 | 8 |
| P5.4 | DxT20P, activate, couple at 6%, <500 kD, >70 kD | 93.4 | 57 | 1000 | 105 | 62 | 21 | 10 | 5 | 3 |
| P4.4 | DxT20P, activate, couple at 6%, <750 kD, >70 kD | 85.1 | 60 | 1300 | 140 | 60 | 36 | 21 | 13 | 7 |
| P4.2 | DxT20P, activate, couple at 6%, <750 kD, >70 kD | 69.8 | 60 | 1000 | 127 | 51 | 30 | 14 | 5.5 | 3 |
| P1.3S | DxT20P, activate, <300 kD, couple at 2%, <750 kD | 74.4 | 60 | 700 | 117 | 35 | 25 | 10 | 3.5 | 1 |
| P1.2S | DxT20P, activate, couple at 2%, <750 kD | 83.6 | 70 | 1300 | 130 | 25 | 24 | 10 | 4 | 2 |
| Samples with acceptable ESR values (3): | | | | | | | | | | |
| P5.2 | DxT20P, activate, couple at 1%, <500 kD, >70 kD | 77.0 | 53 | 500 | 107 | 1-32 | 15 | 5 | 1 | 0.5 |
| P3.4 | DxT20P, activate, couple at 6%, <500 kD, >70 kD | 60.0 | 64 | 700 | 110 | 1-20 | 19 | 6 | 2 | 1 |
| P8.1 | DxT20P, activate, couple at 1%, <500 kD | 91.1 | 53 | 500 | 104 | 1-18 | 15 | 5 | 1.5 | 1 |
| P5.6 | DxT20P, activate, couple at 1%, <500 kD, >70 kD | 74.1 | 52 | 400 | 90 | 1-9 | 7 | 2 | 1 | 0 |
| P102 | DxT20P, activate, <300 kD, couple at 1%, <500 kD, >80 kD | 97.7 | 62 | 400 | 121 | 1 | 18 | 7 | 0.5 | 0 |
| P6.4 | DxT20P, activate, <500 kD, couple at 1%, <500 kD | 93.2 | 52 | 700 | 102 | 2 | 17 | 6 | 2.5 | 1 |
| P6.2 | DxT20P, activate, <300 kD, couple at 1%, <500 kD | 99.3 | 50 | 500 | 96 | 1 | 9 | 2 | 0.5 | 0 |
| P6.8 | DxT20P, activate, <500 kD, couple at 1%, <500 kD | 80.1 | 50 | 700 | 93 | 1 | 11 | 3 | 1 | 0.5 |
| P8.3 | DxT20P, activate, couple at 1%, <500 kD | 83.2 | 50 | 450 | 91 | 1 | 5 | 1 | 0 | 0 |

TABLE 3-continued

Preparation Procedures for Dx-Hb and Analytical Results:

| Batch Code | Procedures & Coupling Conditions (1) | Component Yield (2) | Lower Limit | Upper Limit | Ave MW | ESR mm/hr | % >200 kD | % >300 kD | % >400 kD | % >500 kD |
|---|---|---|---|---|---|---|---|---|---|---|
| P6.6 | DxT20P, activate, <300 kD, couple at 1%, <500 kD | 99.1 | 49 | 500 | 89 | 1 | 9 | 2 | 0.5 | 0 |

Notes:
(1): The coupling of Dx Hb indicates a % value which corresponds to the concentration of Hb. For example, for batch 5.5, the DxHb coupling was effected with 1% Hb and 0.33% DxBr.
(2): Normalized yield of the final DxHb fractionation step, showing the % component of the Dx-Hb produced.
(3): Table 3 includes data sorted by ESR values and indicates a "cut-off" where ESR values are acceptable as defined above.

The following examples serve to illustrate the preferred embodiments of the invention and are not intended to limit the invention in any way.

EXAMPLE 1

Preparation of Stroma-Free Human Hemoglobin (SFH)

SFH of the present invention was prepared according to the method described above. Outdated human blood was supplied by the Hong Kong Red Cross Blood Transfusion Service. Fifteen units (about 4.5 liters) of whole blood, type A, AB, or O, were pooled and mixed with 4.5 L of 10 mM PBS (phosphate buffered saline—a mixture of 10 mM sodium phosphate buffer and 154 mM NaCl), pH 7.4 in a 10-liter glass bottle. The red blood cells (RBC) were washed with 7 volumes of chilled buffer by diafiltration with a hollow fiber filter of 0.65 µm (CFP-6-D-6A) mounted on FlexStrand™ (A/G Technology Corp., Needham, Mass.) at a constant volume of about 10 L. RBC were then lysed slowly with hypotonic 10 mM phosphate buffer at the same pH with a 0.1 µm membrane cartridge (CFP-1-E-6A, A/G Technology Corp). The volume of RBC corpuscle was washed thoroughly with up to 5 volume of the buffer. The filtrate was then diafiltrated through a 500 kD filter (UFP-500-E-5A, A/G Technology Corp.) to assure stroma-free and then concentrated to 20 g/dL by circulating through a 10 kD membrane cartridge (UFP-10-E-9A, A/G Technology Corp.). The solution was diafiltrated with 10 mM PBS, pH 7.4, which was the final storage buffer. The sterility of the final hemoglobin solution was further ascertained by passing through a pre-filter and a 0.22 µm filter (293 mm, Millipore) in series. The stroma-free hemoglobin solution was bottled and stored at 4° C.

EXAMPLE 2

Activation of Dextran by the Alkylation Method

Description of dextran activation by the alkylation method according to the preferred embodiment of the present invention includes small-scale and pilot-scale activation. Small-scale dextran activation may result in the production of DxHb only in limited amounts that is enough for research purposes only, while pilot-scale dextran activation procedure can be used in the industrial setting for the subsequent conjugation of DxHb in larger amounts.

a) Small Scale Activation 0.3 g cyanogen bromide (CNBr) (Riedel-de Haen) dissolved in 3 mL of acetonitrile was added to 95 mL of 2% dextran (mean MW 20 kD, Pharmacia), and the activation was allowed to proceed for 5 minutes. During the activation, pH is maintained at 10.8 by continuous addition of 1 M NaOH. Afterwards, it was lowered to 2.0-2.5 with 2 M HCl. Then, 2mL of diaminoethane (Sigma) was added along with additional HCl to prevent the pH from exceeding 9.5. After stirring at 4° C. overnight, the mixture was thoroughly dialyzed against distilled water. Completeness of dialysis was preferably confirmed by testing the dialysate with the ninhydrin method. Aminoethylamino-dextran was thus obtained Solid $Na_2HPO_4$ was then added into the mixture to a concentration of 0.1 M and pH 7.0, and 3 mL of bromoacetyl bromide (Fluka) was added over a period of 2 hours, accomplished with vigorous stirring and maintenance of pH at 7.0 by addition of 1 M NaOH. Then, the mixture was again dialyzed against distilled water. Completeness of dialysis was preferably confirmed by testing the dialysate with silver nitrate solution. After dialysis, the product N-bromoacetyl-aminoethylamino-dextran (DxBr) was lyophilized and stored in freezer, ready for use.

b) Pilot Scale Activation

Twenty-eight grams of CNBr (Riedel-de Haen) were dissolved in 50 mL of acetonitrile, which was then added to 4.0 L of 3.5% dextran (Pharmacia). The pH of the solution was maintained at 10.8 by continuous addition of 6 M NaOH (about 50 mL) for 5-10 minutes. Afterwards, about 50 mL of 6 N HCl was added to lower the pH to around 2.0. Then, 210 mL of diaminoethane (Sigma) was added along with 6 N HCl (about 500 mL) to keep the pH below 9.5. After stirring at 4° C. overnight, the mixture was thoroughly diafiltrated against 40 L of distilled water with Millipore Pellicon Cassette Filter Acrylic Holder and three stacking PTGC 0005 cassettes (Millipore) at a flow rate of around 8 L per minute. The circulation of the dextan solution was maintained by the use of a Cole-Parmer peristaltic pump (model 7549-40) with an Easy-load pump head (Model 7529-80, MasterFlex). The circulating volume was kept at 3-4 L. To monitor the completeness of the dialysis, the filtrate was then subjected to the ninhydrin test as described below.

Later, 180 mL of bromo-acetyl bromide (Fluka) was added slowly accompanied with vigorous stirring over a period of two hours, during which the solution was maintained at neutral pH by adding 6 M NaOH. Then, the mixture was thoroughly dialyzed with the Pellicon cassette against distilled water (about 50 L). Completeness of dialysis was confirmed by subjecting the filtrate to the silver nitrate test as described below. The activated bromodextran was lyophilized and stored at −20° C.

c) Ninhydrin Test

Firstly, ninhydrin solution was prepared as previously described by Moore, S. and Stein, W. H. (J. Biol. Chem., 1948, 176:367-388; incorporated herein by reference). In short, ninhydrin solution was prepared by mixing 1.0 L of 4.0 M sodium acetate, pH 5.5 with 3.0 L of ethylene glycol monomethyl ether (Sigma). The mixture was bubbled with nitrogen for an hour. Then, 80 g of ninhydrin (Sigma) and 7.5 mL of 21% titanous chloride solution (Sigma) were added. The ninhydrin solution was kept under nitrogen.

To carry out the test, 1.0 mL of ninhydrin solution was mixed with 1.0 mL of the DxBr solution and the mixture was allowed to react at 100° C. for 15 minutes. A blue coloration which could be stabilized by adding 2.0 mL of 50% ethanol indicated a positive result. Quantitative analysis was obtained spectrophotometrically at 570 nm. Ethylamine was employed for calibration. Absence of amino group which would result in colorless solution indicates the thoroughness of the reaction.

A simpler ninhydrin test could be performed to obtain qualitative results, where 1.0 g ninhydrin (Sigma) is dissolved in 50 mL distilled water. One half mL of this ninhydrin solution is mixed with an equal volume of the DxBr solution. The mixture would turn yellow if there were any residual amino groups.

d) Silver Nitrate Test The test was performed by using a silver nitrate ($AgNO_3$) (Nalcalai Tesque) solution. The bromo groups were first released by alkaline hydrolysis. Three drops of 1 M NaOH were added to each of 0.5 mL DxBr samples and the solutions were incubated at 37° C. for 30 minutes. Subsequently, three drops of concentrated nitric acid were added, followed by another three drops of 1% $AgNO_3$ solution. A white precipitate of silver bromide would result if bromide is present, and the solution would turn milky. In the actual experiment described above, there was no white precipitate, which indicated the absence of the bromo group in DxBr solution.

EXAMPLE 3

Preparation of Dextran-Hemoglobin Conjugates

According to the present invention, the conjugation reaction was preferably performed by dissolving 16.7 g of DxBr in 5 L (0.33% DxBr) of 1% stroma-free hemoglobin solution. Sodium bicarbonate buffer was added to a final concentration of 0.1 M and the pH adjusted to 9.5 with 1 M NaOH. The solution mixture was first sterilized by passing through a 0.22 μm filter (Millipore), stirred and the coupling reaction was allowed to proceed at 4° C. for up to 16 hours.

16 mM β-mercaptopropionic acid (Sigma, pH adjusted to 0.5 with NaOH) were added to react with any residual bromo groups and to stop the coupling reaction. The solution was subjected to dialysis against 10 mM phosphate buffered saline, pH 7.4, 60 minutes later to clear any residual reactants such as β-mercaptopropionic acid, bromo groups, etc. A conventional dialysis bag was employed in small test tube scale, while a 10 kD filter cartridge (UFP -10-E-9A, A/G Technol.) was used for the diafiltration in pilot-scale

EXAMPLE 4

Molecular Weight Measurement: Calibration of the Filtration Column

Figure 2:
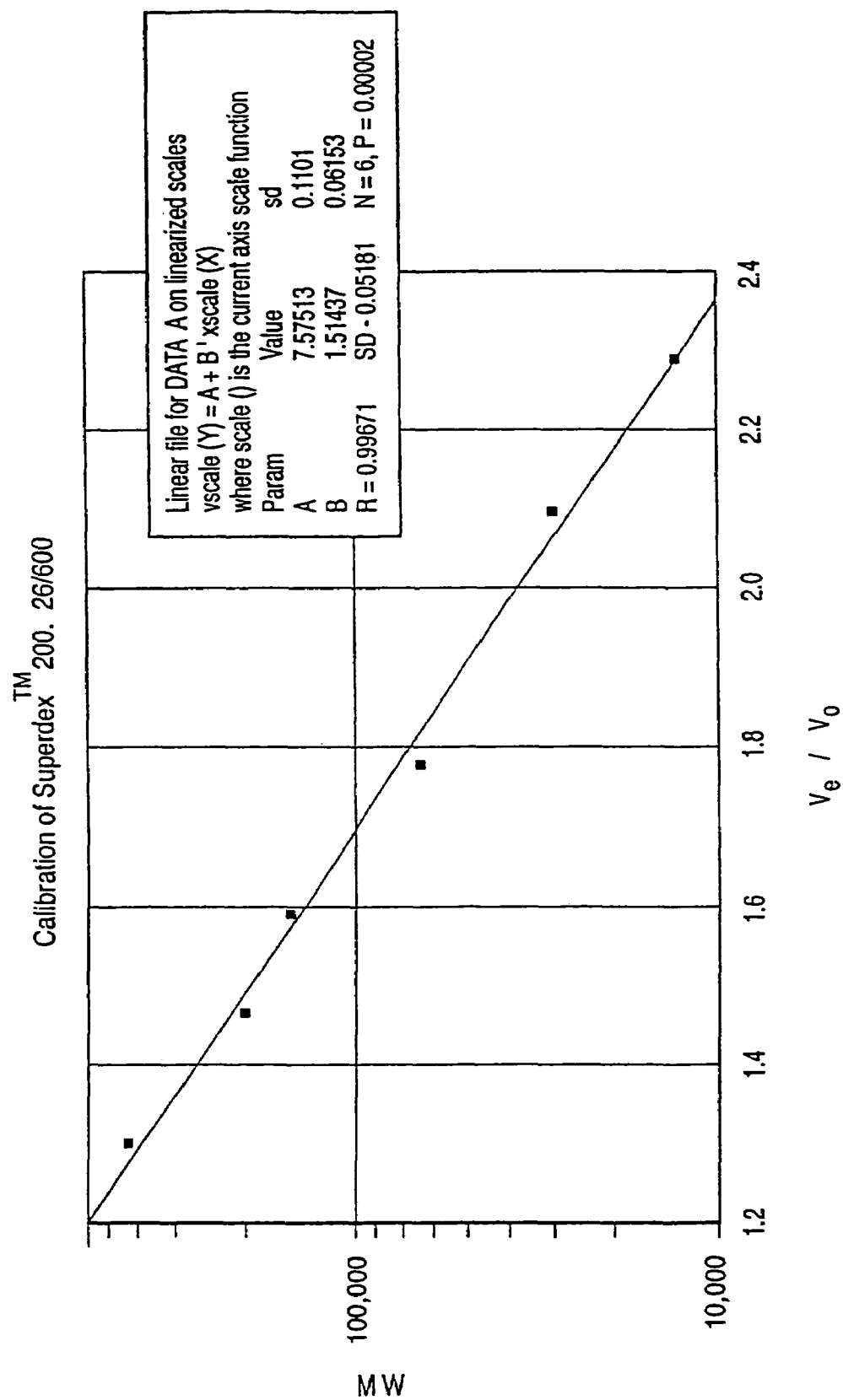
FIG. 2 illustrates a calibration of gel filtration column, Superdex™ 200, 26/600 with standard proteins.

The preferred procedure for determining molecular weights of DxHb preparations of the present invention using gel filtration chromatography is outlined in Technical Bulletin No. GF-3, Sigma Chemical Company, October 1987. Superdex™ 200, 26/600 gel filtration column (Pharmacia) was employed. The column was calibrated with standard proteins before the MW was determined for DxHb conjugates of the present invention. The standard proteins employed were as follows: cytochrome c (MW 12.4 kD), carbonic anhydrase (MW 29 kD), albumin (MW 66 kD), alcohol dehydrogenase (MW 150 kD), β-amylase (MW 200 kD), ferritin (MW 440 kD). The calibration curve is shown in FIG. 2, where molecular weight is plotted versus $V_e/V_o$ for each respective protein standard. The average molecular weight was determined for each fraction since each fraction may contain DxHb of various MW values.

EXAMPLE 5

Development of Hemorrhagic Model in Guinea Pig Method

Six normal, healthy Guinea pigs were used in the optimization of bleeding conditions to develop a useful hemorrhagic model to study the effect on survival and assessment of delivery of oxygen to tissues. Guinea pigs was housed for at least 1 week before experimentations. Food and water were supplied et libido.

The animals were anaesthetized with intraperitoneal (i.p.) injection of pentobarbital, as it is known that Guinea pigs have narrower respiratory tracts and ether is to be avoided. The jugular vein and carotid artery were cannulated for infusion of control or testing solution and blood pressure was measured with a pressure transducer connected to an electronic amplifier and a 10 mV recorder respectively. The animal was bled at a rate of 30%, 50%, 70%, 90%, and 100% of Maximum Bled Out for the first 10 minutes, then at smaller volumes of about 0.2-0.5 ml occasionally to keep the blood pressure low. The blood volume bled was calculated as follows:

| Total blood volume (TBV) | = | body weight (g) × 8% |
|---|---|---|
| Maximum Bled Out (MBO) | = | TBV × 60% |
| 10-minute Bled Out (10BO) | = | MBO × various percentage |

After bleeding and maintaining at a low blood pressure of about 25 mmHg for 90 minutes, 0.2 ml of blood was drawn for lactate determination with a serum lactate kit (Sigma). Procedures indicated on the Sigma diagnostic kits were followed. Briefly, blood was mixed with equal volume of TCA solution, centrifuged after standing for several minutes. The supernatant stored for later lactate assay. Blood vessels were tied, and the wound was rinsed with ampicillin and sutured. The animals were then monitored and survival and body weight data were recorded. Animals that lived longer than 7 days were classified as "survivors".

Results and Conclusion

The following results of survival and 90-minute blood lactate levels were obtained:

| 10BO (% MBO) | >7-Day Survival (%) | 90-min Serum Lactate (mg/dl) | Standard Error |
|---|---|---|---|
| 0 | 100 | 6.2 | 1.3 |
| 30 | 83.3 | 32.2 | 10.0 |
| 50 | 58.3 | 44.8 | 26.4 |
| 70 | 27.3 | 62.1 | 16.3 |
| 90 | 8.3 | 77.5 | 26.3 |
| 100 | 0.0 | 115.1 | 32.5 |

Figure 4:
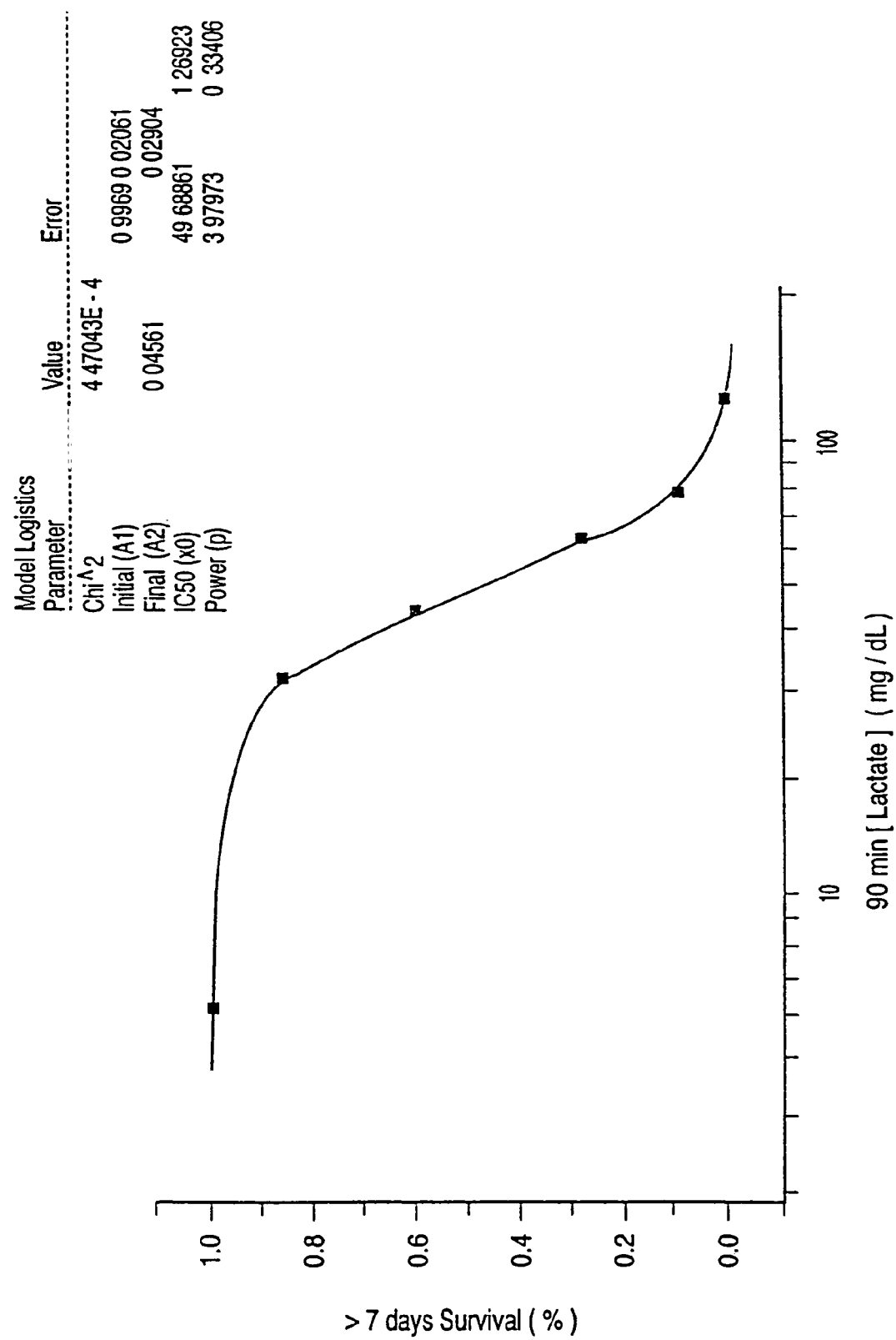
FIGS. 4 and 5 illustrate the results of the experiments of Example 5.
Figure 5:
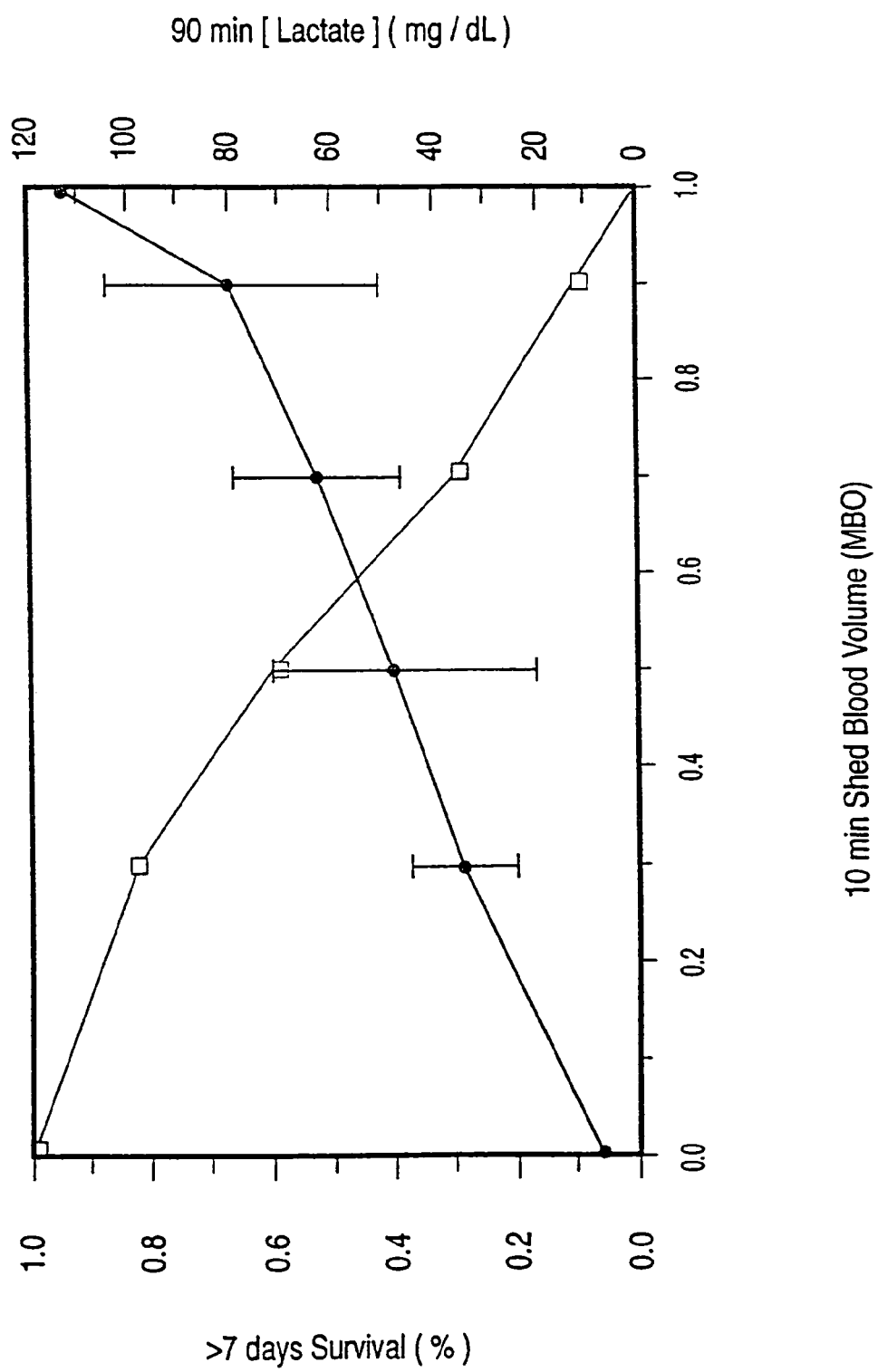

FIGS. 4 and 5 illustrate the effect of 10-minute bled out volume on the long-term survival of the hypovolemic shocked animals and the relationship between the survival outcome and the 90-minute lactate levels. Generally speaking, the faster the bleeding, the higher the lactate level, suggesting anaerobic respiration of the animal, and that the animal was in a hypovolemic shock state. Furthermore, the higher the lactate level, the lower the long-term survival. Survivors can live for longer than 2 more months after experimentation and gradual weight gain was observed. On the contrary, if the animal did not recover, weight loss continued and eventually it would die within the first few days.

Results and Conclusion

| Test Solution | n | Survival (%) |
|---|---|---|
| Kidney dialysis fluid (KDF) | 7 | 75.0 |
| 5% Hb (#29) in KDF | 6 | 50.0 |
| 5% Dx(ZHB)-Hb > 70 kD | 6 | 83.3 |
| 5% Dx(ZGB)-Hb > 70 kD | 6 | 66.7 |
| 5% Dx(DBB)-Hb > 70 kD | 5 | 60.0 |
| 5% Dx(DBB)-Hb > 70 kD | 6 | 16.7 |
| 5% Dx(DBB)-Hb 70-300 kD in KDF | 9 | 77.8 |
| 5% Dx(DDB2)-Hb 70-500 kD in KDF | 9 | 100.0 |
| 5% Dx(DBB)-Hb 70-500 kD in KDF | 8 | 87.5 |
| 5% Dx(DBB)-Hb 70-750 kD in KDF | 4 | 50.0 |
| 5% Dx(DBB)-Hb 70-1,000 kD in KDF | 9 | 66.7 |
| 5% Dx(DBB)-Hb 70-1,000 kD in KDF | 5 | 20.0 |
| 5% Dx(DDB)-Hb > 1,000 kD in KDF | 3 | 0.0 |

Description of DxHb conjugates used:

| | Dextran Brand | Dextran Size (MW) | Volume | Dextran Weight (g) | CNBr Weight | Diamino-ethane | Bromoacythyl-bromide | Yield (%) |
|---|---|---|---|---|---|---|---|---|
| ZGB | Fisons | 20,000 | 5 L | 120 g | 24 g | 180 ml | 180 ml | 63% |
| ZHB | Fisons | 20,000 | 5 L | 120 g | 24 g | 180 ml | 180 ml | 100% |
| DBB | Phamacia | 20,000 | 5 L*7 | 143 g*7 | 28 g*7 | 210 ml*7 | 210 ml*7 | 94% |
| DDB | Phamacia | 20,000 | 5 L*15 | 66 g*15 | 10 g*15 | 100 ml*15 | 125 ml*10 | 82% |
| DDB2 | | | | | | | | 75% |

DDB2: derived from DDB with a <500K A/G cartridge.

EXAMPLE 6

Resuscitation with Dextran-Hemoglobin Solution after an otherwise Fatal Hemorrhage in Guinea Pig Method Commercially available Guinea pigs of body weights between 350 and 550 gm were fasted overnight (16 hrs) and then anesthetized with pentobarbital (Sigma) by intraperitoneal injection. The level of anesthesia was assessed by the response to hind toe pinch and a sufficient response was continuously maintained by further doses of pentobarbital injection. The carotid artery was cannulated for bleeding and arterial blood pressure measurement with a pressure transducer connected to an electronic amplifier and a 10 mV chart recorder. The jugular vein was cannulated for fluid infusion.

A volume equivalent to 70% of MBO was bled through the carotid artery during the first 10 minutes, during which time the blood pressure changed from 85 mmHg to 30 mmHg. Subsequently, 0.2-0.5 ml was bled occasionally for the following 80 minutes to keep the blood pressure at 25-30mmHg. At 90 minutes, a bled volume of control buffer, hemoglobin (Hb) or fractionated dextran-hemoglobin (Dx-Hb) in kidney dialysis fluid was infused over 60 minutes. Only those with a 90-minute lactate level between 50-90 mg/dl were included, because too low or excessively high lactate level might be brought about by inconsistence of bleeding skill during the experimentation.

It will be understood by persons skilled in the art that the DxHb conjugates of the present can be used for a variety purposes and in a variety of manners. Primarily, the conjugates of the present invention can be used as blood substitute or blood expander. By way of example, the DxHb conjugates can be used as a blood substitute to prevent hemorrhagic shock (in trauma wards) or for hemodialysis.

Although the invention has been described with reference to certain specific embodiments, various modifications thereof will be apparent to those skilled in the art without departing from the spirit and scope of the invention as outlined in the claims appended hereto.

REFERENCES

The following is a listing of some of the references that have been discussed above. The contents of the following are incorporated herein by reference.

1) Chien, S., and K-M. Jan. (1973) Ultrastructural basis of the mechanism of rouleaux formation. *Microvasc. Res.* 5:155-166.

2) Chien, S., S. A. Luse, K-M. Jan, S. Usami, L. H. Miller, and H. Fremount. (1971) Effects of macromolecules on the rheology and ultrastructure of red cell suspensions. *6th Europ. Conf Microcirc.* pp.29-34.

3) Dintenfass, L. eds. (1985) Blood viscosity, hyperviscosity & hyperviscosaernia. Boston:MTP Press, pp.45-112.

4) Dintenfass, L. eds. (1981) Hyperviscosity in Hypertension. Sydney:Pergamon Press, pp.140.

5) Fabry, T. L. (1987) Mechanism of erythrocyte aggregation and sedimentation. Blood 70:1572-1576.

6) Izumida, Y., A. Seiyama, and N. Maeda. (1991) Erythrocyte aggregation: Bridging by macromolecules and electrostatic repulsion by sialic acid. *Biochim. Biophys. Acta* 1067:221-226.

7) Jan, K-M. (1979) Red cell interactions in macromolecular suspension. *Biorheology* 16:137-148.

8) Tam, S-C., J. Blumenstein, and J. T. Wong. (1978) Blood replacement in dogs by dextran-hemoglobin. *Can. J. Biochem.* 56:981-984.

9) Tam, S-C., J. Blumenstein, and J. T. Wong. (1976) Soluble dextran-hemoglobin complex as a potential blood substitute. *Proc. Natl. Acad. Sci. USA* 73:2128-2131.

10) Tsai, S. P., and J. T. Wong. (1996) Enhancement of erythrocyte sedimentation rate by polymerized hemoglobin. *Artif. Cells Blood Substitutes Immobilization Biotechol.* 24:513-523.

11) Wong, J. T. (1988) Rightshifted dextran-hemoglobin as blood substitute. *Biomater. Artif. Cells Artif. Organs* 16:237-245.

We claim:

1. A method for preparing an oxygen carrying compound, said compound comprising a conjugate of hemoglobin covalently bound to a dextran molecule, said method comprising:

1) reacting the dextran with a bromine compound to provide bromine containing groups on said dextran, thereby providing an activated dextran;

2) filtering of said activated dextran with a first filter having a pore size that results in a retentate having a molecular weight greater than 500 kD;

3) reacting the activated dextran filtrate of step (2) with hempglobin therby providing a conjugated dextran-hemoglobin molecule;

4) filtering said dextran-hemoglobin molecule with a filter having a pore size that reults in a retentate having a molecular weight greaterthan 500 kD, and further filtering through a filter having a pore size that results in a filtrate containing molecules having a weight greater than 80 kD.

2. The method of claim 1 wherein said dextran has an average molecular weight of 20 kD.

3. The method of claim 1 wherein said first filter has a pore size that results in a retentate having a molecular weight greater than about 300 kD.

4. The method of claim 1 wherein said hemoglobin is stroma-free hemogobin.

* * * * *